(12) United States Patent
Reeve et al.

(10) Patent No.: US 8,237,927 B1
(45) Date of Patent: *Aug. 7, 2012

(54) MULTI-COLOR CAVITY RINGDOWN BASED DETECTION METHOD AND APPARATUS

(75) Inventors: Scott W. Reeve, Jonesboro, AR (US); Susan Davis Allen, Jonesboro, AR (US)

(73) Assignee: Arkansas State University—Jonesboro, State University, AR (US)

(*) Notice: Subject to any disclaimer, the term of this patent is extended or adjusted under 35 U.S.C. 154(b) by 82 days.

This patent is subject to a terminal disclaimer.

(21) Appl. No.: 12/848,816

(22) Filed: Aug. 2, 2010

Related U.S. Application Data

(63) Continuation-in-part of application No. 11/756,876, filed on Jun. 1, 2007, now Pat. No. 7,768,647.

(60) Provisional application No. 60/803,757, filed on Jun. 2, 2006.

(51) Int. Cl.
*G01N 21/00* (2006.01)

(52) U.S. Cl. ......... 356/437; 356/432
(58) Field of Classification Search .......... 356/432–440; 73/23.3, 23.2, 23.31; 250/227.18, 343, 559.4, 250/345, 339.12–339.13
See application file for complete search history.

(56) References Cited

U.S. PATENT DOCUMENTS

| 7,768,647 B2 * | 8/2010 | Reeve et al. ............. 356/437 |
| 2003/0189711 A1 * | 10/2003 | Orr et al. ............. 356/484 |

* cited by examiner

*Primary Examiner* — Tri T Ton
(74) *Attorney, Agent, or Firm* — Joe D. Calhoun; Rashauna A. Norment

(57) ABSTRACT

A multi-color cavity ringdown based spectrometer system is housed in a light tight enclosure to detect the presence of trace quantities of gas phase molecules emanating from a subject, explosives, drugs, or hazardous materials. A method is also disclosed for simultaneous real time detection of gas phase molecules emanating from explosives, drugs, hazardous materials, a subject's breath skin or bodily fluid.

13 Claims, 9 Drawing Sheets

MULTI-COLOR CAVITY RINGDOWN BASED DETECTION METHOD AND APPARATUS

CROSS REFERENCE TO RELATED APPLICATIONS

This is a continuation-in-part application of co-pending U.S. Utility patent application Ser. No. 11/756,876, filed 1 Jun. 2007, now U.S. Pat. No. 7,768,647, which claimed the benefit of U.S. Provisional Application No. 60/803,757, filed 2 Jun. 2006, the disclosures of which are incorporated herein by reference.

FEDERALLY SPONSORED RESEARCH AND DEVELOPMENT

This application contains a subject invention made, in part, with Government support under Contract No. W15P7T-10-C-A012 between the U.S. Army and Arkansas State University.

MICROFICHE APPENDIX

Not applicable.

BACKGROUND OF THE INVENTION (1) Field of the Invention

The present invention relates to molecular absorption spectroscopy methods and apparati, and in particular to those methods and apparati which employ a multi-color optical cavity for increasing detection sensitivity, molecular specifity and discrimination, especially ones adapted for cavity ringdown spectroscopy. Additionally, this invention relates to an enclosure or portal apparatus employing a multi-color optical cavity for increasing detection sensitivity of gas phase molecules. This invention also relates to the detection of at least one gas phase molecule, especially a volatile organic compound or ammonia emanating from human skin, using the same multi-color technology.

(2) Background of the Invention.

The ideal optically based sensor combines a high selectivity towards the species of interest, a low Limit-of-Detection (LOD), and a real time sensing capability. High selectivity can often be obtained by utilizing a narrow-band (high resolution) light source or wavelength selection detection system. Spectroscopically speaking, an optical sensor can operate in either an absorption or emission mode. Certainly, emission based sensors can produce lower limit of detection ("LOD") in many cases. On the other hand, quantifying the spectral intensities from an emission based sensor to extract information regarding species concentrations is challenging due to inherent dynamical effects (quenching, predissociation, unknown quantum yields, etc.).

Direct absorption spectroscopy methods have many experimental advantages including selectivity and ease with which the absorbance measurements can be used to quantify species concentrations. While direct absorption measurements, at least the way in which the standard infrared absorption experiments are performed, do not possess the same level of detection sensitivity as fluorescence spectroscopic methods, there are specialized measures that can be incorporated into the experiment to overcome this limitation. For example, assuming Beer's Law can be applied to the absorption measurement and a previously optimized set of experimental conditions, it should be clear that improvements in the signal to noise ratio for the measurement can be realized by increasing the absorption path length. One strategy therefore, is to incorporate a multi-pass absorption sample cell into the experiment to effectively increase the path length through the sample. Indeed, by interfacing a 32 m White cell with a standard FTIR instrument, Robitaille and coworkers have demonstrated the ability to distinguish, identify and quantify 2,4-DNT, 2,6-DNT, and TNT vapor from heated soil samples with a ppm detection sensitivity. Clapper, M., J. Demirgian, and G. Robitaille, *A Quantitative Method using FTIR to Detect Explosives and Selected Semivolatiles in Soil Samples*, Spectroscopy, 10(7), 44-49 (1995).

Parenthetically, the problem of soil contamination at DOD and DOE facilities apparently represents a significant environmental problem. There are a number of federally funded studies focusing on the development of down-the-hole sensors for a variety of contaminants including explosives. As another example, spectroscopists from Aerodyne Research, utilizing a tunable Pb-salt diode laser coupled to an astigmatic Herriott cell reported both laboratory mechanistic as well as in situ field studies demonstrating a sensitive, specific, real time sensing capability for TNT in soils. Wormhoudt, J., J. H. Shorter, J. B. McManus, P. L. Kebabian, M. S. Zahniser, W. M. Davis, E. R. Cespedes, and C. E. Kolb, *Tunable infrared laser detection of pyrolysis products of explosives in soils*, Applied Optics, 35(21), 3992-3997 (1996). The TNT soil measurements reported in the literature utilized a thermal desorption system to entrain the soil contaminants into the gas phase.

For over two millennia, students of medicine have recognized that odors given off by the body, in particular those odors associated with exhaled breath, could be utilized as an indicator of health. Phillips M, "Detection of volatile organic compounds in breath," In Disease markers in exhaled breath, 219-231. Editors Marczin N, Kharitonov S A, Yacoub M H and Barnes P J. Marcel Dekker, New York, N.Y. (2002). In the last decade, EPA studies have reported that exhaled breath can also be used to assess the exposure of individuals to environmental toxins. Pleil, J. D., "Role of Exhaled Breath Biomarkers in Environmental Health Science," J. Toxicology and Environmental Health, Part B, 11, 613-629 (2008). Indeed, there have been a number of studies examining the history, application, and analysis of breath data for risk assessment purposes. Pleil, J. D., and Lindstrom, A. B., "Sample timing and mathematical considerations for modeling breath elimination of volatile organic compounds," Risk Anal., 18, 573-580 (1998).

However, volatile organic compounds (VOCs) and other trace gases emanating from the human skin have received comparatively less attention, even though it represents a far less invasive sampling method than breath analysis. Similar to the situation with breath analysis, the measurement of trace gases from human skin can be directly correlated with VOC concentration in blood. Zhang, Zho-Min., Cai, Ji-Jin., Harvey, Ruan, Gui-Hua. and Li, Gong-Ke., "The study of fingerprint characteristics of the emanations from human arm skin using the original sampling system by SPME-GC/MS," Journal of Chromatography B, 822,244-245 (2005). These gases rise to the skin surface either through perspiration or directly from the blood via the capillaries under the skin. (Id.)

Skin gas emissions can be difficult to detect since the concentrations are often below the detection limit of many conventional analytical methods. Nonetheless, a recent gas chromatograph—mass spectrometric (GC-MS) study has demonstrated the ability to measure and quantify ammonia in human skin gas. Nose, K., Mizuno, T., Yamane, N., Kondo, T., Ohtani, H., Araki, S., Tsuda, T., "Identification of ammonia in gas emanated from human skin and its Correlation with that in blood," Anal. Sci., 21, 1471-1474 (2005).

Optical sensors designed to detect vapor emissions are not limited in scope or application for explosive or energetic related samples. Many illicit drugs such as heroine or cocaine are often in chloride form. As a result, chlorine-containing compounds will often be detected in the vapor emissions from these compounds. Optically based vapor sensors also have potential applications as a medical diagnostic. There are over 3000 volatile organic compounds (VOC's) in exhaled breath of humans, many of which are also released by the skin or other biological surfaces exposed to air. Gordon, S. M., J. P. Szidon, B. K. Krotoszynski, R. D. Gibbons, and H. J. O'Neill, *Volatile Organic Compounds in Exhaled Air from Patients with Lung Cancer*, Clin. Chem., 31(8), 1278-1282 (1985). The relative concentrations of VOC's have for centuries been used to assist in diagnosis. Patients suffering from diabetes tend to have elevated levels of ketones, principally acetone, in their breath for example, and hence often smell like rotten apples. More recently, patients suffering from breast cancer have been shown to have elevated levels of formaldehyde in their exhaled breath. O'Neill, H. J., S. M. Gordon, M. H. O'Neill, R. D. Gibbons, and J. P. Szidon, *A Computerized Classification Technique for Screening for the Presence of Breath Biomarkers in Lung Cancer*, Clin. Chem., 34(8), 1613-1618 (1988). The challenge for optical sensors in these cases is the ability to differentiate between normal and elevated levels of VOC's in a patient.

There have been multiple recent reports of dogs detecting melanoma in patients, presumably by sensing the emission of characteristic skin gases, and dermatologists are looking at the possibility of detecting other skin cancers via differences in skin gas emission. (Dermatology Blog, Jan. 25, 2009.) Detecting prostate and bladder cancer in patients using dogs to identify VOC biomarkers in urine is also being investigated. (The Baltimore Sun, Jun. 3, 2010.) The present invention concerns the use of a multi-color cavity ringdown based spectrometer system for simultaneous real time analyses of the same gas sample for detection and discrimination of ammonia, VOCs and/or other skin gases, having utility in a variety of applications such as (for example) the diagnosis of health conditions, prescribing the treatment of health conditions, monitoring the treatment of health conditions, and determining a subject's recent exposure to or ingestion of substances that are prohibited or regulated.

For many applications involving energetic materials, illicit substances, or medical diagnostics however, gaining an order of magnitude or two by increasing the absorption path length to 100 m or so may still not be sufficient. Consider that high quality military explosives need not be present in large quantities to cause significant damage particularly if combined with an incendiary compound. Persons with malicious intent can further exacerbate the vapor detection problem by encasing explosives in containers specifically designed to minimize vapor emissions. For medical diagnostic applications, the most useful sensor would be one capable of detecting elevated VOC levels at a pre-symptomatic, i.e., low concentration, stage.

In the late 1980's another direct absorption method was serendipitously discovered that allows absorption path lengths of 10 kilometers to be realized. O'Keefe, A. and D. A. G. Deacon, *Cavity ringdown optical spectrometer for absorption measurements using pulsed laser sources*, Review of Scientific Instruments, 59(12), 2544-2551 (1988). Called cavity ringdown laser absorption spectroscopy or "CRD", by its originators, it involves measuring changes in the characteristic ringdown time of a high Q optical cavity due to the presence of an absorbing sample. The ringdown cell is actually a type of lossmeter that was used initially to determine the reflectivity of high reflectance mirrors (R>99.9%). Over the past decade, cavity ringdown has been exploited by a number of research groups for a variety of applications. See for example, Busch, K. W. and M. A. Busch, Editors, *Cavity-Ringdown Spectroscopy: An ultratrace Absorption Measurement Technique*, ACS Symposium Series 720, American Chemical Society, Washington, D.C. 1999 and references therein. There have even been some preliminary studies to examine the potential of cavity ringdown for trace detection of explosive materials. Steinfeld, J. I., R. W. Field, M. Gardner, M. Canagaranta, S. Yang, A. Gonzalez-Casielles, S. Witonsky, P. Bhatia, B. Gibbs, B. Wilkie, S. L. Coy, and A. Kachanov, *New Spectroscopic Methods for Environmental Measurement and Monitoring*, SPIE, 3853, 28-33 (1999); Todd, M. W., R. A. Provencal, T. G. Owano, B. A. Paldus, A. Kachanov, K. L. Vodopyanov, M. Hunter, S. L. Coy, J. I. Steinfeld, and J. T. Arnold, *Application of mid-infrared cavity-ringdown spectroscopy to trace explosives vapor detection using a broadly tunable (6-8 µm) optical parameteric oscillator*, Applied Physics B, 75, 367-376 (2002); and Usachev, A. D., T. S. Miller, J. P. Singh, F.-U. Yueh, P.-R. Jang, and D. L. Monts, *Optical Properties of Gaseous 2,4,6-Trinitrotoluene in the Ultraviolet Region*, Applied Spectroscopy, 55(2), 125-129 (2001).

In the classic cavity ringdown experiment, a pulsed laser system serves as the radiation source. O'Keefe, A. and D. A. G. Deacon, *Cavity ringdown optical spectrometer for absorption measurements using pulsed laser sources*, Review of Scientific Instruments, 59(12), 2544-2551 (1988); and Busch, K. W. and M. A. Busch, Editors, *Cavity-Ringdown Spectroscopy: An ultratrace Absorption Measurement Technique*, ACS Symposium Series 720, American Chemical Society, Washington, D.C. 1999 and references therein. Output from this pulsed laser source is injected in a cavity consisting of two highly reflective mirrors (R>99.99%). Once injected into the cavity, the light pulse can traverse the cavity thousands of times, although a small portion of the intensity of the pulse leaks out of the cavity as each mirror is encountered. A detector is situated behind the minor opposite the radiation input to monitor cavity output and/or decay of the laser pulse. For pulsed light sources, whose coherence length is short compared to the physical size of the cavity, the decay is typically exponential and possesses a decay or ringdown time characteristic for the cavity. In the presence of absorbing species, this characteristic ringdown time changes and hence absorption spectroscopy can by performed by measuring the difference in ringdown time as a function of molecular species concentration. For cavities with highly reflective mirrors, the absorption path length can approach 10 kilometers. The ultra-trace vapor detection potential of cavity ringdown is due then to this tremendous gain in path length compared with more traditional spectroscopic methods.

Prior CRD detection methods are deficient in that each of the methods take too much time to be useful in a real world environment. In the classic CRD laser experiment, an absorption spectrum, plotted as the intensity loss of the cavity versus wavelength, is actually composed of a great many individual cavity ringdown events. Collection of the absorption spectra or scan is initiated by first tuning the laser (or some other optical source) to a starting wavelength for the scan. A ringdown event is observed, averaged, and then modeled as an exponential decay in order to extract a characteristic ringdown time for the cavity at this starting wavelength and in the presence of an absorbing sample to be analyzed. Finally, this wavelength specific ringdown time, $\tau_{sample}(\lambda_{start})$, is compared with the ringdown time for an evacuated cavity, again at a specific wavelength, $\lambda_{start}$. This difference, $\beta = \tau_{empty}(\lambda_{start}) - \tau_{sample}(\lambda_{start})$, represents the first ordered pair in the absorption spectrum ($\beta_{start}, \lambda_{start}$). Of course an absorption spectrum includes a large number of such pairs. To continue collecting a spectrum, the laser must then be stepped or tuned to a new wavelength and the process repeated until an entire absorption spectrum has been obtained. Depending upon the size of the wavelength region to be scanned and/or the size of the individual steps for each retuning, such an experimental scheme can become quite time intensive (to the point of becoming time prohibitive for a real time sensor).

Driven by the molecular sensing potential of CRD methods, there have been a number of attempts to circumvent the time intensive nature involved with the collection of an absorption spectrum via the CRD method (which does not include the subsequent principal component analysis step required to quantify trace amounts of species in the gas sample). In some cases, a single averaged, wavelength specific, CRD event, chosen to coincide with the linecenter for a strong absorption peak in the spectrum, is used to perform the detection and quantification analysis. See for example, Wang, C., S. T. Scherrer, and D. Hossain, *Measurements of Cavity Ringdown Spectroscopy of Acetone in the Ultraviolet and Near-Infrared Spectral Regions: Potential for Development of a Breath Analyzer*, Applied Spectroscopy, 58(7), 784-791 (2004). Unfortunately, this strategy can severely limit the selectivity of the CRD method and, particularly for real world samples which can contain hundreds of compounds, effectively cripples the usefulness of the CRD approach. Other attempts to circumvent the time intensive collection challenge involve the use of a broadband laser or optical source. See for example, Scherer, J. J., J. B. Paul, H. Jiao, and A. O'Keefe, *Broadband ringdown spectral photography*, Applied Optics, 40(36), 6725-6732 (2001); and Biennier, L., F. Salama, M. Gupta, and A. O'Keefe, *Multiplex integrated cavity output spectroscopy of cold PAH cations*, Chemical Physics Letters, 387, 287-294 (2004). Indeed, O'Keefe and coworkers have demonstrated that such broadband light sources can in fact generate optical spectroscopic data for molecular species present only in trace amounts and in essentially real time. Scherer, J. J., J. B. Paul, H. Jiao, and A. O'Keefe, *Broadband ringdown spectral photography*, Applied Optics, 40(36), 6725-6732 (2001); and Biennier, L., F. Salama, M. Gupta, and A. O'Keefe, *Multiplex integrated cavity output spectroscopy of cold PAH cations*, Chemical Physics Letters, 387, 287-294 (2004). The trade off, of course, is that their broadband approach cannot achieve the same level of spectral resolution (and hence selectivity) as a narrow band laser source. In another incarnation of the broadband CRD concept, the output of a CRD cell was sent to a monochromator equipped with a diode-array or CCD detector. See Fiedler, S. E., A. Hese, and A. A. Ruth, *Incoherent broad-band cavity enhanced absorption spectroscopy*, Chemical Physics Letters, 371, 284-294 (2003); and Gherman, T. and D. Romanini, *Mode-locked cavity-enhanced absorption spectroscopy*, Optics Express, 10(19), 1033-1041 (2002). Both groups have reported broadband CRD spectra with spectral resolution on the order of several tenths of a wavenumber resolution; certainly sufficient to rotationally resolve the molecules studied in these reports ($O_2$-Ruth and $C_2H_2$-Romanini) Unfortunately, this level of spectral resolution is insufficient to produce rotationally resolved spectra for larger molecules and, moreover, the experimental scheme described in these reports is not readily transferable to the fingerprint region of the infrared, primarily due to performance characteristics of monochromators, spectrographs, and linear array detectors. The above discussed technical problems can be solved by the following apparatus. In essence a series of cw diode lasers, quantum cascade lasers, or other tunable laser sources, each tunable over a discrete, yet unique, fingerprint region of the infrared, will provide a capability to not only take advantage of the inherent sensitivity of the cavity ringdown method, but will also provide a high level of selectivity by allowing numerous fingerprint regions to be examined simultaneously. A PZT actuated mirror mount on each CRD cavity in the multi-color sample cell can facilitate use of these cw light sources. To ensure reliable and robust operation of the cavity ringdown instrument when interfaced with a scalable screening portal or other sampling device, hollow glass waveguides (HGW's) and/or infrared fiber optics can be utilized to interface each laser with the cavity ringdown detection cell. One of the limitations that has always been cited when comparing infrared or near infrared cavity ringdown methods with other infrared spectroscopic methods such as FTIR, is that while FTIR is orders of magnitude less sensitive, one can acquire a spectrum of the fingerprint region in less time. The invention disclosed herein effectively represents a solution to this limitation by allowing the measurement of multiple discrete fingerprint wavelengths simultaneously.

SUMMARY OF THE INVENTION

To achieve greater molecule specificity and LOD sensitivity for detection and monitoring of skin gas, as well as add a real time capability, the invention disclosed herein includes (comprises) a multi-color optical spectrometer including a tunable mid IR laser (such as a Pb-salt diode laser or quantum cascade laser, for example) coupled with a shared gas sample space, to perform real time detection and/or diagnostic and/or monitoring measurements. A multi-color cavity ringdown based spectrometer is housed in a light tight enclosure to detect the presence of trace quantities of gas phase molecules of compounds of interest entering the enclosure. In one embodiment of the invention, the compounds are explosives or drugs being transported through the enclosure. In another embodiment of the invention, the compounds are compounds contained in the exhaled breath of a person breathing into the enclosure. In another embodiment, the gas sample is collected from the skin of the subject being examined. In another embodiment, the gas sample is collected from the urine or other bodily fluid of the subject being examined. In another embodiment all emissions are collected from a subject in a cabinet-like enclosure by flowing a small amount of air over the person. Skin gases are collected by condensation from the gas stream at a low temperature, then analyzed using the multiwavelength spectrometer. This latter embodiment collects both skin and breath emissions at the same time.

More specifically, the output from a laser source is coupled into a multi-color cavity ringdown sample cell by launching the radiation into a series of optical elements designed to match the optical mode characteristics of the CRD cavity, hereinafter, the telescope. Simultaneous ringdown measurements at multiple wavelengths are collected by utilizing a series of at least two cavity ringdown analysis systems, each having matched cavity ringdown cavities made of a pair of astigmatic highly reflective mirrors coated for a specific region of the infrared. The invention provides a broadband/multi-color capability through the use of several Pb-salt diode or quantum cascade ("QC") lasers, or other tunable lasers, each designed to lase in a different spectral region. Each individual laser is coupled with a different set of CRD mirrors, optimized with a reflectivity bandwidth for that particular laser all mounted on a single gas sample cell. A telescope is included to mode match the radiation with the individual cavity ringdown cavities.

To circumvent the time intensive protocol associated with generating a CRD absorption spectrum for the gas sample, i.e., observation of a wavelength dependent ringdown event, average, analyze, retune/step laser to next wavelength, observe wavelength dependent ringdown event, etc., we combine a multi-color laser approach with the ICOS method of O'Keefe et. al. O'Keefe, Scherer, and Paul, U.S. Pat. No. 6,975,190 B1, 2004; and O'Keefe, A., J. J. Scherer, and J. B. Paul, *CW Integrated Cavity Output Spectroscopy*, Chemical Physics Letters, 307, 343-349 (1999). The ICOS variation of cavity ringdown involves mounting one of the cavity mirrors on a piezoelectric transducer ("PZT") actuated mirror mount. Here the transmission fringe problem can be eliminated through the clever application of an amplitude modulation voltage to the PZT. Thus, linear cavity ringdown absorption spectra can be obtained with cw laser sources using the ICOS method without the need for expensive acousto-optic modulators or other optical isolating devices. By rapidly scanning each individual laser over a single longitudinal mode an absorption spectrum for all regions of spectroscopic interest with detection sensitivities similar to those afforded by the more traditional CRD methods is obtained.

This approach is different from the other previously disclosed multi-color and/or multiplexed diode laser instruments. See for example, Totschnig, G., D. S. Baer, J. Wang, F. Winter, H. Hofbauer, and R. K. Hanson, *Multiplexed continuous-wave diode laser cavity ringdown measurements of multiple species*, Applied Optics, 39(12), 2009-2016 (2000). In the case of Hanson and coworkers, they describe a system consisting of two near infrared diode lasers of nearly identical wavelength output and perform their experiment by sequentially sending radiation from first one laser and then the other through a single set of CRD mirrors. Both Hanson et. al. and Lukow describe a experimental protocol incorporating the observe, average, analyze, and retune approach to performing the CRD measurements. Totschnig, G., D. S. Baer, J. Wang, F. Winter, H. Hofbauer, and R. K. Hanson, *Multiplexed continuous-wave diode laser cavity ringdown measurements of multiple species*, Applied Optics, 39(12), 2009-2016 (2000); and Lukow, http://chem.tufts.edu/PropDataBase/Stefan Prop-.pdf, 2002. Neither of these approaches appears to have a real time capability, effectively limiting their potential as a molecular sensor.

Another distinguishing aspect of this approach is the molecular species used in the sensing process. In the case of explosive and/or energetic compounds, most approaches tend to focus on the spectral signature for the pure energetic material. Many of these explosive compounds have extremely low vapor pressures making the challenge of detecting the pure material quite significant. Moreover, explosive devices are often enclosed in hermetic containers and/or hidden effectively lowering the material's vapor pressure by several orders of magnitude making detection of even an explosive such as TNT (trinitrotoluene), which possesses a relatively high vapor pressure at room temperature (10 parts per billion by volume), well beyond the limits of current technology. To circumvent this seemingly insurmountable challenge, the approach described here can utilize a series of characteristic signatures for explosive detection in addition to or instead of utilizing the signature of the substance itself. These characteristic signatures are due to naturally occurring impurities in energetic compounds and are believed to constitute the bouquet of odors trained canines use for locating, identifying, and detecting explosives. In the case of TNT based explosives, this bouquet is composed of spectral signatures from toluene, nitrobenzenes (principally the mono- and di-variations), and nitrotoluenes (there are several mono- and di-structural isomers). For RDX based explosives (including C4), cyclohexanone appears to be the primary constituent of the bouquet. Acetone is the species to be sensed for TATP (triacetone triperoxide) based explosives.

The rotationally resolved spectral signatures for many of these explosive bouquet compounds are not currently available in the literature. As part of this approach a spectroscopic library containing the required spectral information is currently being developed for sensing applications. Most of these bouquet molecules are not only classified as asymmetric tops, they are fairly large molecules from a high resolution spectroscopy perspective. Obtaining rotationally resolved spectra for such molecules is often impossible without utilizing molecular beam and/or supersonic jet cooling techniques. However we were able to obtain rotationally resolved infrared spectra for a number of these explosive bouquet molecules as well as identify a number of wavelength regions suitable for sensing applications without jet cooling methods by spectroscopically measuring these bouquet compounds at trace concentration levels with a long pathlength absorption cell. Under these conditions, only the most intense spectral features can be observed. The individual spectra shown in FIGS. 5-8 represent the first reported rotationally resolved infrared measurements for toluene, nitrobenzene, and o-mononitrotoluene in the 650-750 $cm^{-1}$ region (Ford and Reeve, in press).

Medical diagnostic applications represent a different sort of challenge from those described above for explosive detection. For biomedical sensing, the instrument must not only be capable of detecting trace amounts of biomarkers the complicated matrix of exhaled breath, but must also possess the sensitivity to distinguish between normal levels and elevated levels of a particular biomarker. Although in some cases, the biomarkers for medical diagnostic applications are similar to those in explosive detection. For example, acetone is both a target for TATP detection and sensing as well as being a biomarker for diabetes in humans.

BRIEF DESCRIPTION OF THE DRAWINGS

These and other features, aspects and advantages of the present invention will become better understood with regard to the following description, appended claims and accompanying drawings, wherein:

DETAILED DESCRIPTION OF THE INVENTION

For the sake of simplicity and to give the claims of this patent application the broadest interpretation and construction possible, the following definitions will apply:

The term "skin gas" essentially means any gas phase molecule emanating or otherwise exiting from a subject organism (including fluids thereof), especially from the outermost layer of cells of a subject organism (regardless of whether such layer of cells qualifies as dermis or skin or mucous membrane); skin gas may include ammonia, volatile organic compounds or any other gas phase molecule exiting a subject organism (or any fluid thereof).

Figure 1:
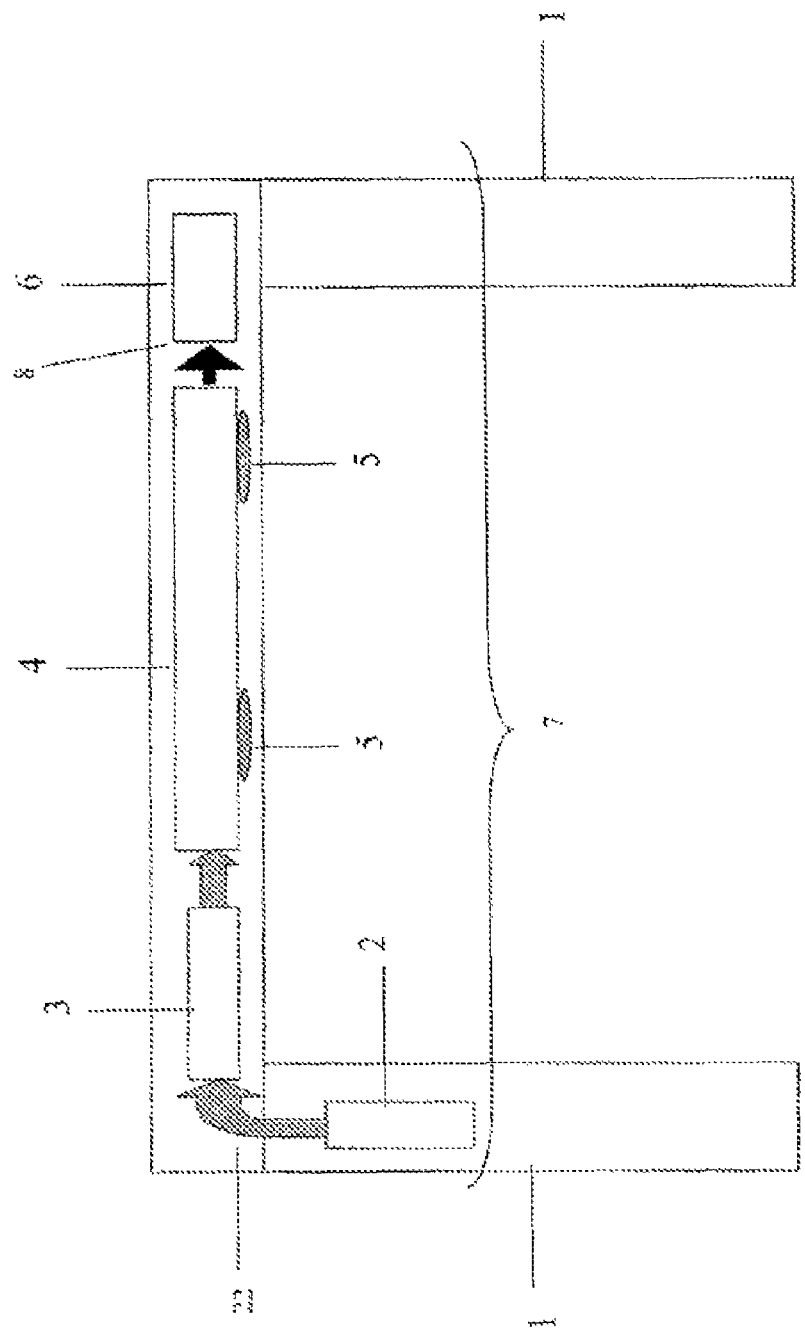
FIG. 1 is an overall schematic of the invention depicting a detection enclosure of unspecified dimensions.
Figure 2:
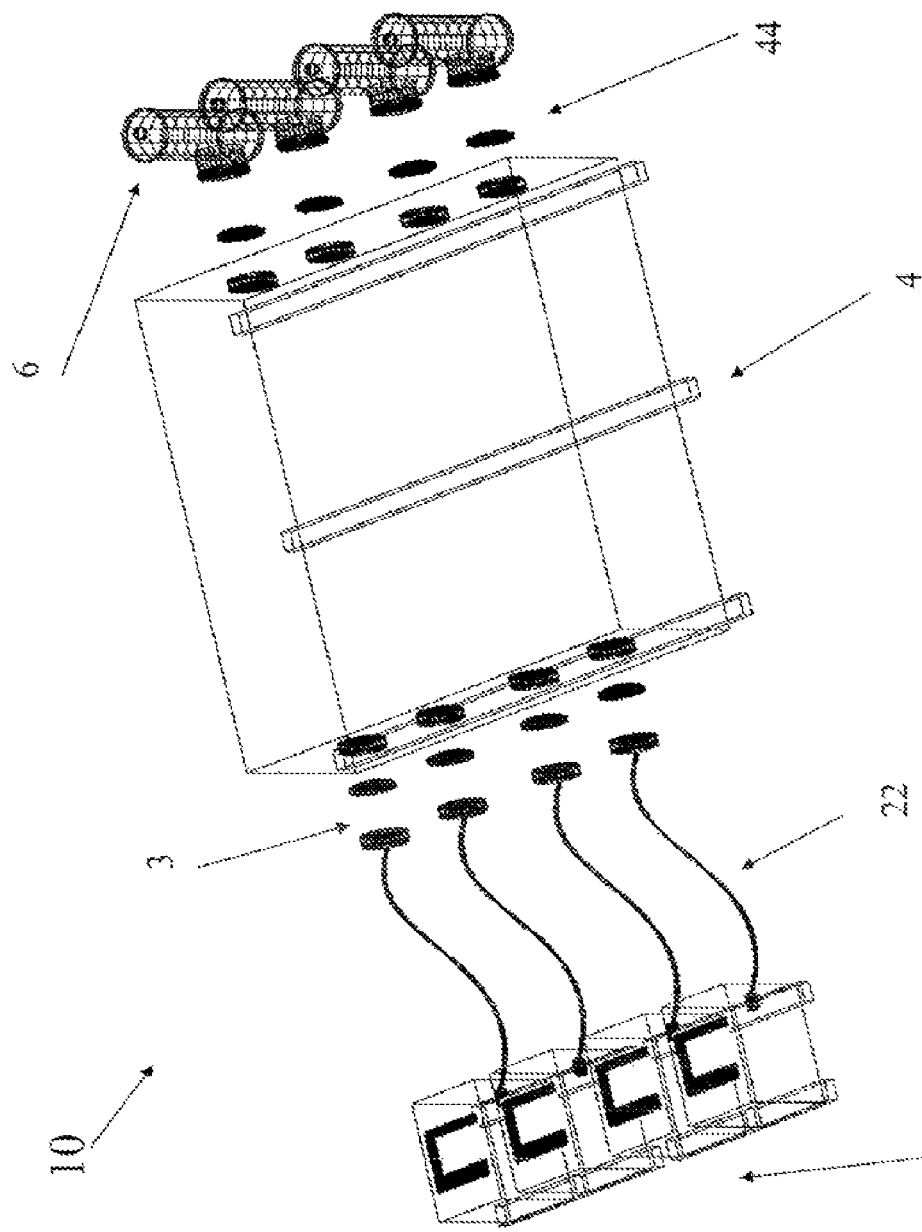
FIG. 2 is a schematic is an expanded view of the cavity ringdown detection spectrometer inside the enclosure.

In FIGS. 1 and 2 there is illustrated a multi-color absorption spectroscopy apparatus 10 for detecting certain molecules in the gas phase, made of a set of at least two cavity ringdown analysis systems 7, a photometric detector 6 to receive and analyze radiation emitted from each of the cavity ringdown cells 4 in the cavity ringdown analysis systems 7, and means 5 for receiving a gas into cavity ringdown laser-based detection cells, hereinafter "cavity ringdown cells" 4 in the cavity ringdown analysis systems 7 for analysis. FIG. 2 shows four cavity ringdown analysis systems 7 with photometric detectors 6. A cavity ringdown analysis system 7 made of a laser 2 emitting radiation at a wavelength, means 22 for transporting the radiation from the laser; a telescope 3, receiving the radiation from the means 22 for transporting and emitting the radiation, and a cavity ringdown cell 4, receiving the radiation from the telescope 3 and emitting the radiation to go to the photometric detectors 6. The wavelengths of the radiation emitted from each of the lasers 2 are different.

In the preferred embodiment of the invention, the apparatus 10 described above is either contained in a light tight enclosure 1 as displayed in FIG. 1 wherein the light tight enclosure 1 has means to receive gas phase emissions or contained in a light tight enclosure 1 attached to a tube, not shown, into which a user could breathe to introduce breath to be analyzed into the apparatus. Below, the device and how it works are described in more detail.

Now referring to FIG. 1, a light tight enclosure 1 is shown. In one embodiment, the light tight enclosure 1 is of sufficient size to receive an, object (not, shown) to be analyzed for at least one gas phase molecule. Dimensions can be scaled to allow the light tight enclosure 1 to scan cargo/vehicles as well as individuals. The object to be analyzed can be a vehicle, such as a truck, a container, such as a shipping container, or individuals. In another embodiment, the enclosure 1 can be connected to a tube (not shown) to receive the exhaled breath of a user (not shown) to be analyzed for at least one gas phase molecule. The term at least one gas phase molecule means that at least one specific type of molecule can be detected. Housed within the light tight enclosure 1 is a set of at least two cavity ringdown analysis systems 7, each made of a cavity ringdown cell 4 and telescope 3, a laser 2 emitting radiation at a wavelength, sample collection and preparation apparatus 5, light detectors 8 and associated photometric detectors 6. The light tight enclosure 1 includes a set of at least two different color lasers 2. In the preferred embodiment, the different color lasers are Pb-salt diode lasers or quantum cascade lasers. The set of at least two different color lasers 2 is operationally connected to a set of telescopes 3. There is one telescope 3 connected to each laser 2. The function of each telescope 3 is to couple the radiation into the cavity ringdown cell 4. The radiation can enter the telescope 3 by a means 22 for transporting the radiation from the laser 2; for example a hollow glass waveguide or appropriate fiber optic cable. While conventional optics could be also be used to transport the radiation, in the preferred embodiment, fiber optics (or a set of HGWs) give the device added robustness. The cavity ringdown cell 4 including a means 5 to receive a gas phase sample. While a chromatography and/or separation method for removing water and other interfering materials from species of interest could, in principle, be used for this purpose, in the preferred embodiment the means 5 to receive a sample includes at least one molecular sieve and a pre-concentrator bar, as described below, to direct selected materials into the cavity ringdown 4. Additionally, this apparatus 10 includes a set of at least two photometric detectors 6 for photometric detection of at least one chemical molecule. There is one detector 6 for each laser 2.

FIG. 2 is a schematic in an expanded view of the apparatus 10 from the set of at least two different color lasers 2 to the cavity ringdown cell 4 inside the light tight enclosure 1 showing the set of at least two different color lasers 2, the means 22 for transporting the radiation from the laser, which could be, for example, hollow glass waveguides and/or fiber optics to guide the laser radiation to the telescope 3, and the cavity ringdown cell. All of the lasers 2 will have output in the mid-infrared region of the electromagnetic spectrum, also known as the fingerprint region.

Figure 3:
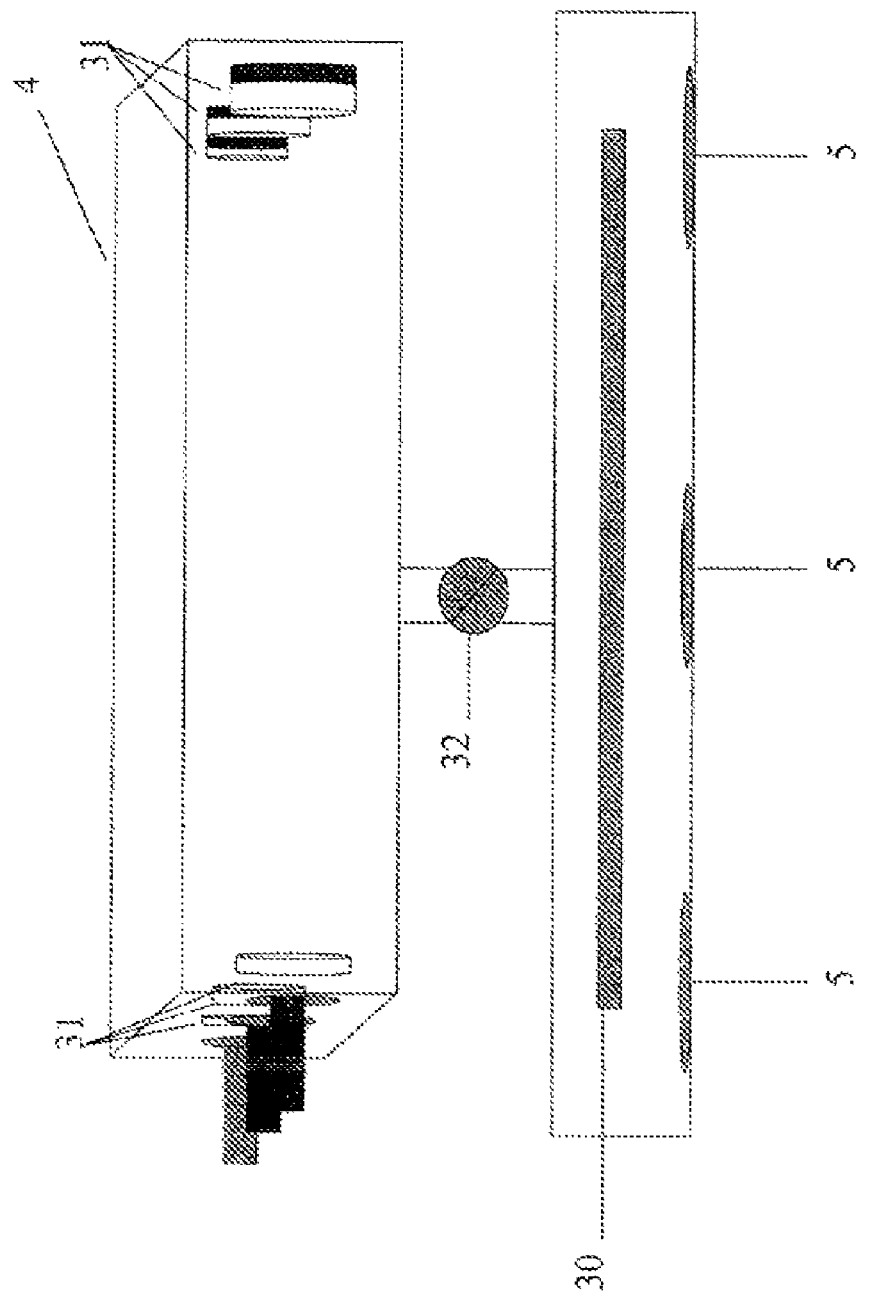
FIG. 3 is a schematic drawing of the cavity ringdown detection cell.

FIG. 3 shows the cavity ringdown detection cell 4 containing a number of sets of astigmatic mirrors 31 each optimized for a different region in the infrared. There will be one set of mirrors 31 (representing an individual cavity ringdown cavity) for each laser 2. In the preferred embodiment, the means 5 to receive a gas phase sample will be effectuated as follows: air samples to be analyzed will first be passed through a set of molecular sieves 5 and will then interact with a sample preparation apparatus 30, i.e. a pre-concentrator bar. This sample preparation apparatus 30 will have the capability to be sequentially cooled to trap materials to be detected and then flash heated to inject these materials into the cavity ringdown cell 4 through valve 32 for identification and quantification of molecular species present.

Figure 4:
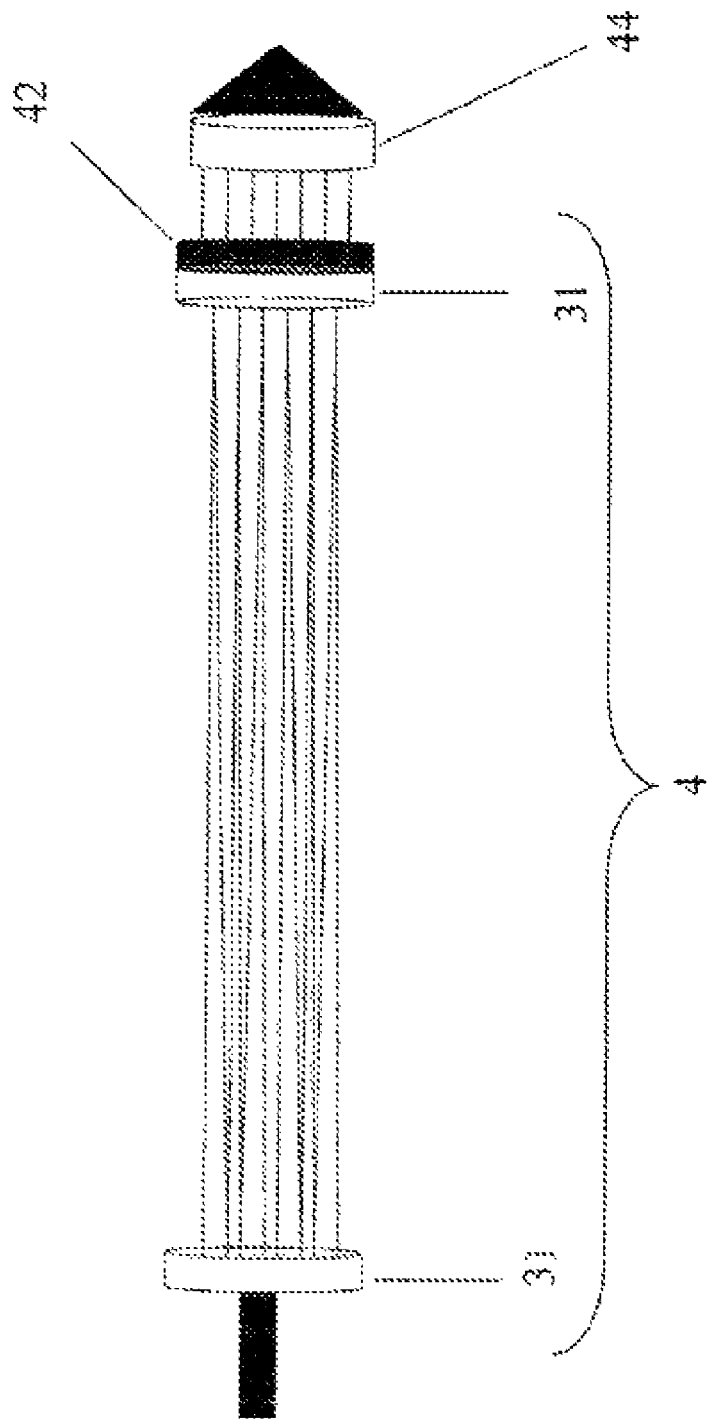
FIG. 4 is a schematic and schematic drawing of an individual cavity ringdown cell.

FIG. 4 shows one of the individual sets of astigmatic mirrors 31 mounted within the cavity ringdown cell 4. Note the PZT actuate mirror mount 42 on one of the mirrors. Following the cw ICOS approach to cavity ringdown introduced by Paul, Scherer, and O'Keefe, U.S. Pat. No. 6,795,190 column 4 line 65 through column 9 line 22 (hereby specifically incorporated by reference in its entirety) the effective cavity length of each individual cavity ringdown cavity is modulated over a number of cavity modes while rapidly scanning each diode laser through a single longitudinal mode. Upon exiting the cavity cell 4, the radiation is focused through a lens 44 onto a standard photometric detector 6. In the preferred embodiment, the detector is a Mercury Cadmium Telluride ("MCT") detector. Detector signals are sent to a computer for further analysis.

The spectral analysis issue warrants some additional explanation. In the classic cavity ringdown experiment, a series of ringdown events, obtained over a sequential set of wavelengths, constitutes an absorption spectrum. Actually it is the change in the characteristic ringdown time for a cavity containing an absorbing species (compared to that of an empty cavity) that is the quantity of interest from a spectroscopic perspective. Thus, the absorption spectrum can be defined as a plot change in ringdown time for the cavity versus wavelength. With an absorption spectrum in hand, standard methods for extracting concentrations are readily available. See for example, Bernath, P. F., Spectra of Atoms and Molecules, Oxford University Press, New York, N.Y. 1995. Of course, generating an absorption spectrum in the classic cavity ringdown manner can be a time consuming undertaking to the point of being time prohibitive for the applications described in this disclosure. For many ultra-trace detection applications, many published reports describe using a ringdown event at a single wavelength (albeit one corresponding to an absorption maximum for the species of interest) to circumvent the time prohibitive limitation. Unfortunately, this strategy may not be effective for a real world sample containing potentially interfering (but yet innocuous) compounds.

The invention addresses this potentially challenging limitation in two fundamental ways. First, using the modified cavity ringdown method of O'Keefe et. al. O'Keefe, Scherer, and Paul, U.S. Pat. No. 6,975,190 B1, 2004; and O'Keefe, A., J. J. Scherer, and J. B. Paul, *CW Integrated Cavity Output Spectroscopy*, Chemical Physics Letters, 307, 343-349 (1999), known as ICOS, absorption spectra are collected by modulating both the cavity ringdown cell mirror and the diode laser albeit with detection sensitivity inherent with the cavity ringdown absorption technique. Second, the invention can collect ICOS absorption spectra for several different fingerprint regions of the infrared simultaneously by simultaneously modulating or scanning several different lasers. In other words, this invention does not suffer from the potential time prohibitive limitation of other previously published cavity ringdown embodiments, while at the same time it retains the high degree of selectivity inherent in Pb-salt diode and/or quantum cascade laser systems. Finally, the invention can utilize a unique approach for the sensing of explosive compounds by focusing on vapor signatures from a series of naturally occurring impurities in the explosives in addition to or instead of the pure explosive material itself. In essence, the invention is designed to mimic the trained canine nose in terms of molecular species used to produce an alert or positive response and represents a fundamental shift in optically based explosive sensing design and development.

Figure 5:
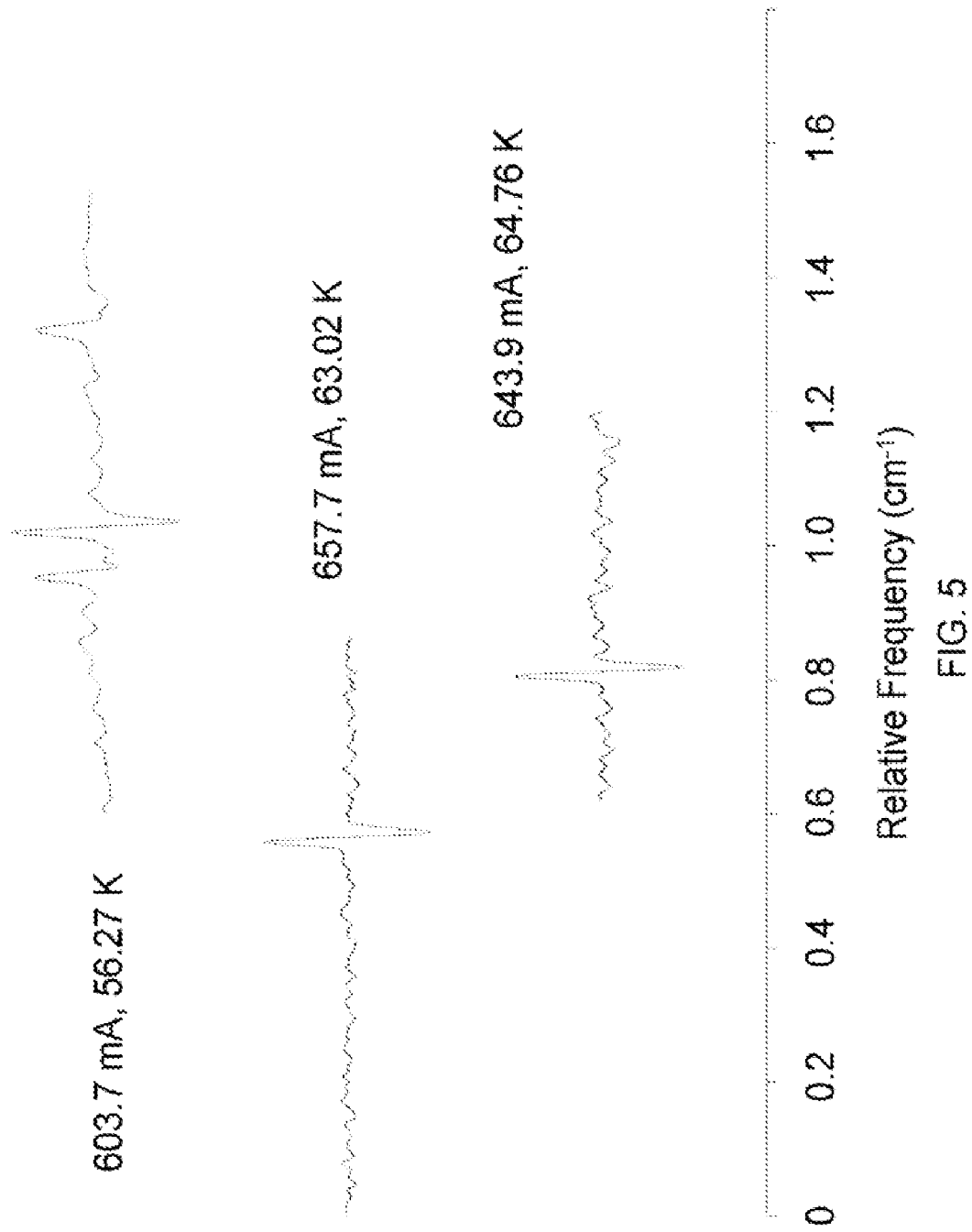
FIG. 5 shows several discrete portions of the rotationally resolved vibrational spectrum of toluene in the 13-15 micron range. Each trace represents a first derivative single scan (no signal averaging) over a distinct longitudinal mode of a Pb-salt laser. The traces are plotted in terms of relative frequency for convenience. The starting point for each scan appears offset due to the differences in longitudinal lasing mode characteristics and the manner in which an automated LabVIEW calibration routine operates. Pb-salt diode laser current and temperature settings are also listed for each scan.
Figure 6:
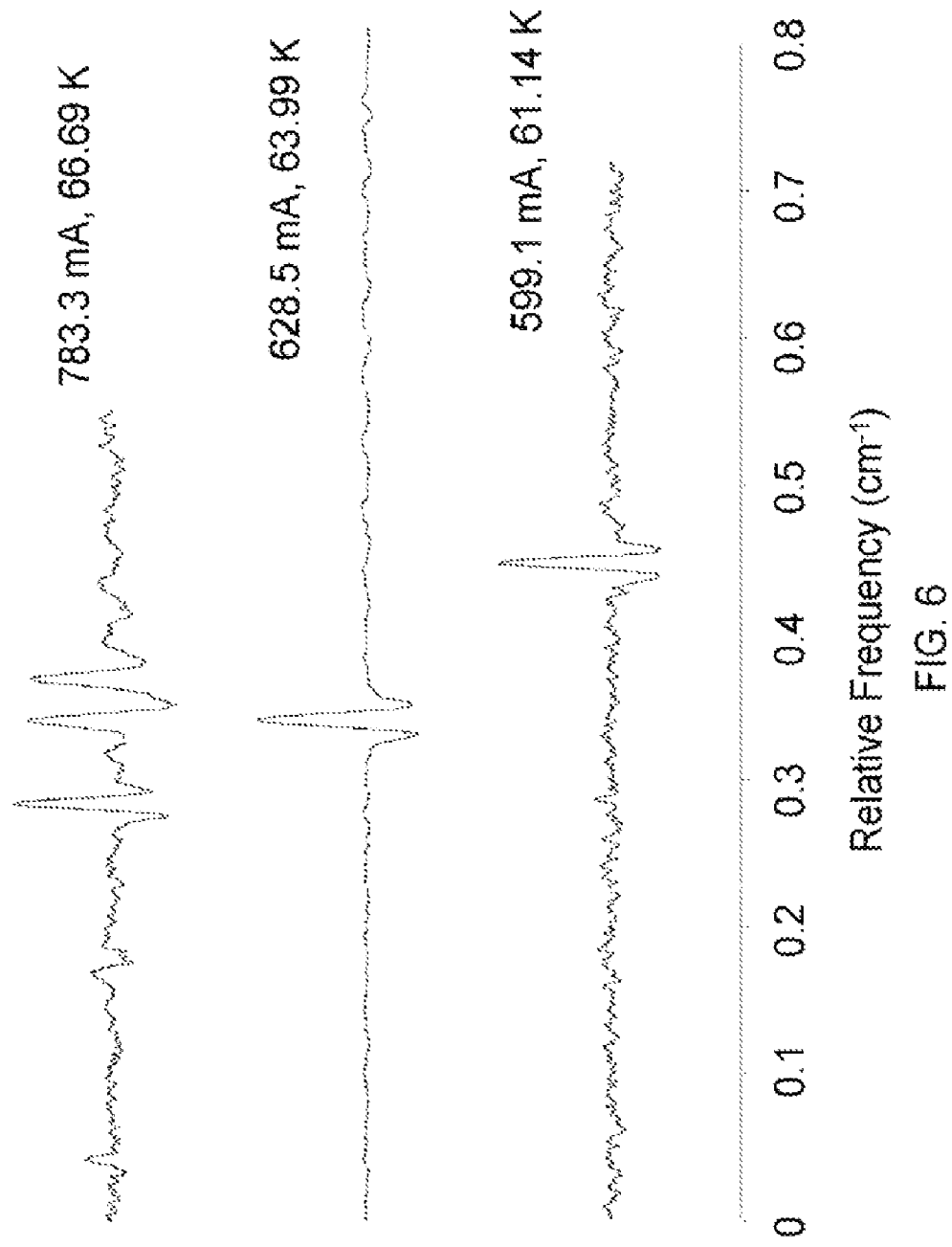
FIG. 6 shows several discrete portions of the rotationally resolved ring bending mode for nitrobenzene in the 13-15 micron region.
Figure 7:
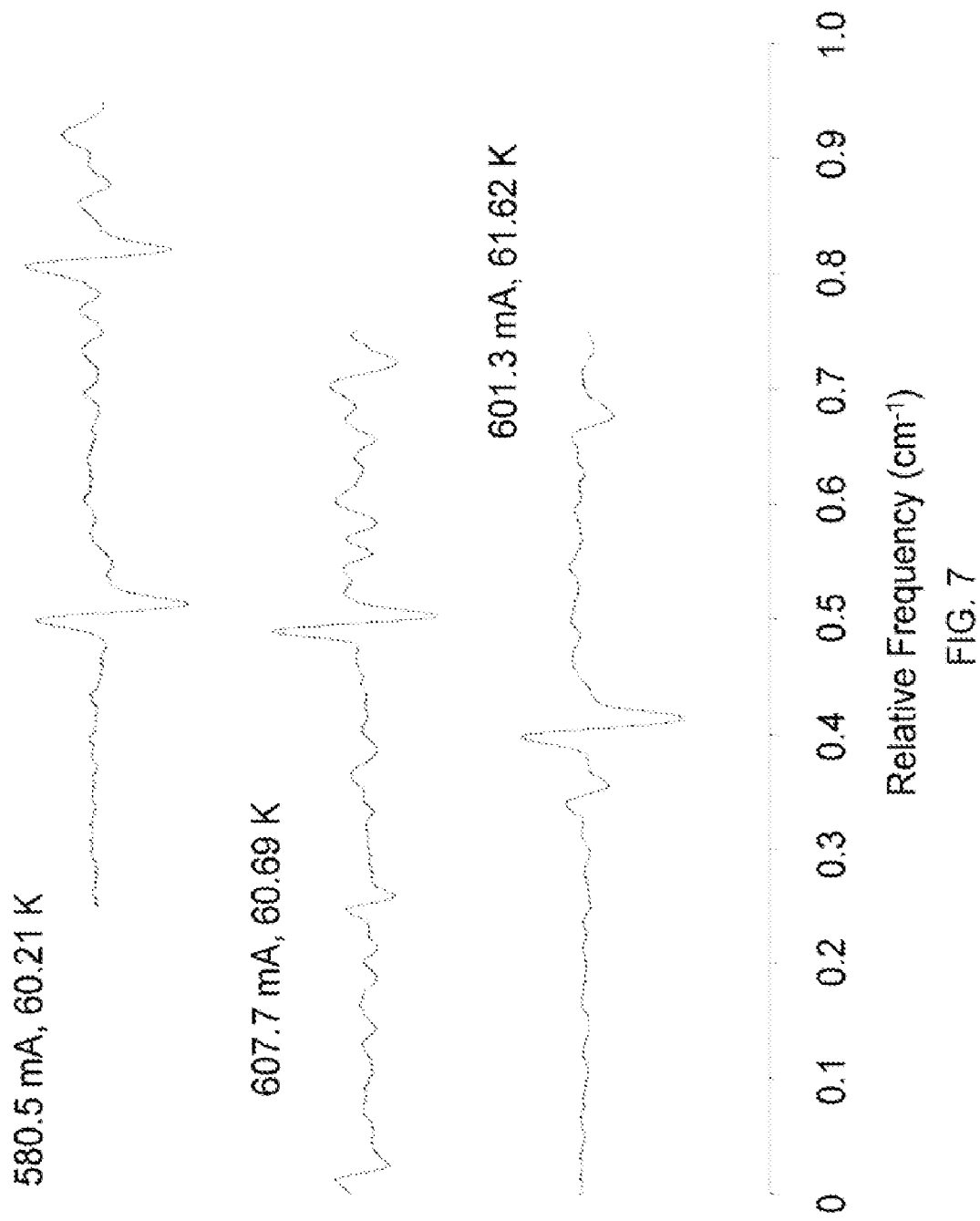
FIG. 7 shows several discrete portions of the rotationally resolved ring bending mode for o-mononitrotoluene in the 13-15 micron region.
Figure 8:
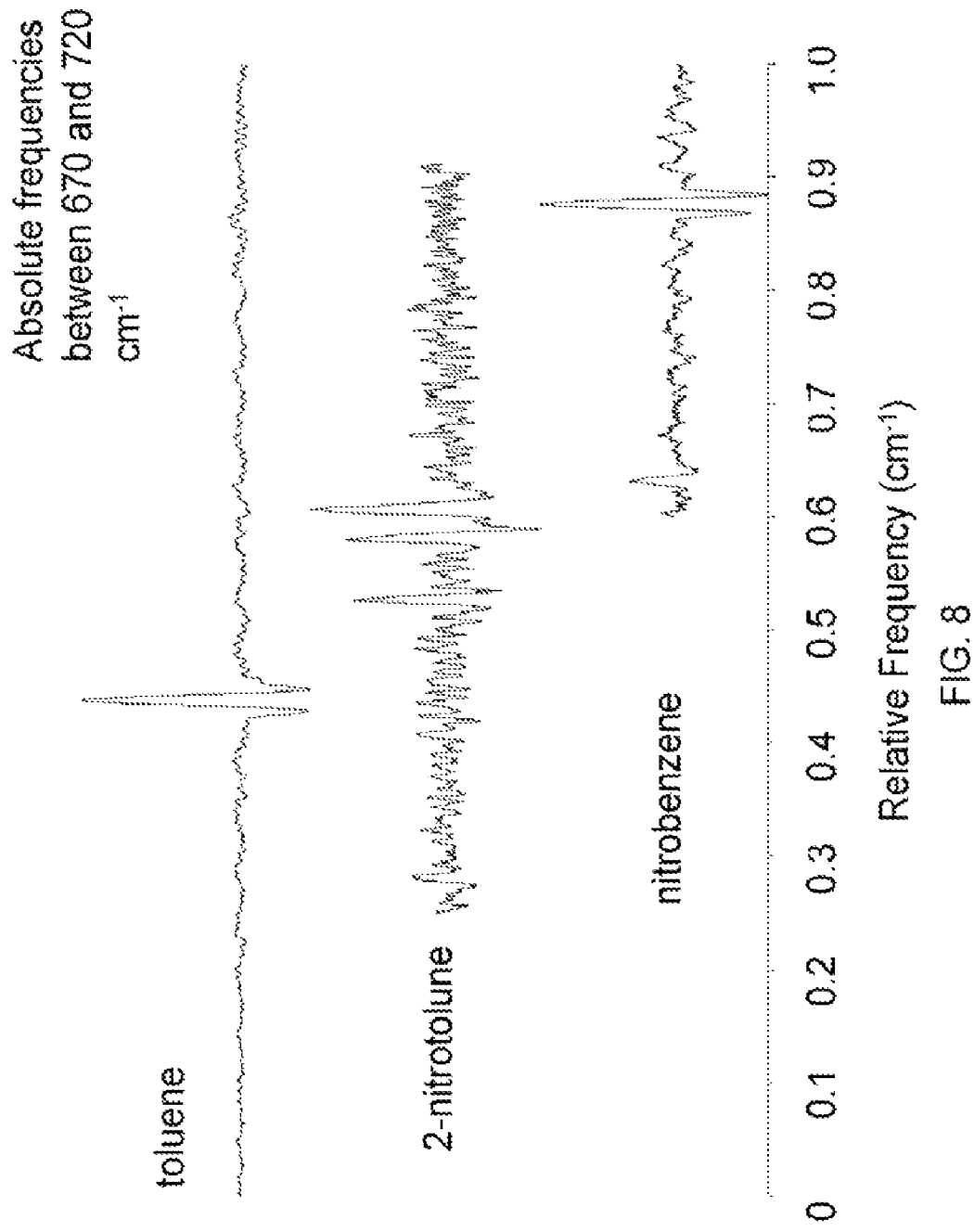
FIG. 8 shows a series of second derivative rotationally resolved absorption measurements obtained with a simulated explosive bouquet sample in the 13-15 micron range. The top trace is due to toluene in the sample, the middle trace nitrobenzene, and the bottom trace is an o-mononitrotoluene signature. The data was collected by sequentially tuning a single Pb-salt diode laser appropriate wavelength regions for each species in the bouquet.
Figure 9:
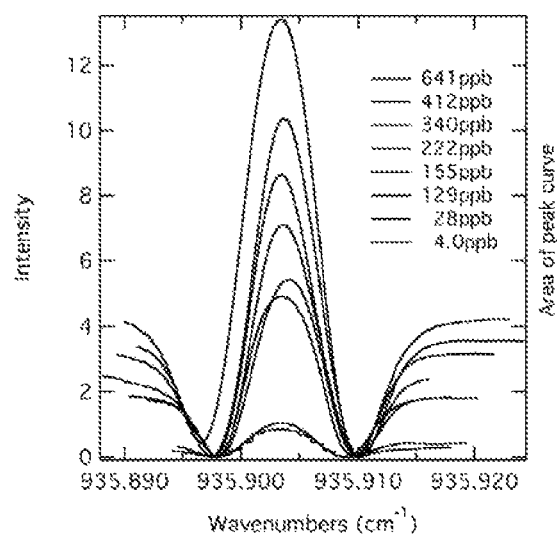
FIG. 9 depicts the calibration curve and signal $^{Q}Q$ (7,3) transition of ammonia in spectral traces of different $NH_3/N_3$ concentration and/or mixtures.

In FIGS. 5, 6, and 7, portions of the spectroscopic database for toluene, nitrobenzene, and o-mononitrotoluene, collected with a single Pb-salt diode laser system, are shown. Each of these traces depicts spectral regions that could potentially be utilized for sensing applications. To date, dozens of spectral transitions have been measured, catalogued and recorded for toluene, nitrobenzene, o-mononitrotoluene, and m-nitrotoluene. Ford, A. R. and S. W. Reeve, *Sensing and Characterization of Explosive Vapors near 700 $cm^{-1}$*, SPIE Proceedings, 6540, in press. To demonstrate the utility of this approach, FIG. 8 shows a series of traces obtained by sequentially tuning a single Pb-salt diode laser to sensing regions for toluene, nitrobenzene, and o-nitrotoluene. The measurements in FIG. 8 were performed on a simulated explosive bouquet created by bubbling a 1000 ppm toluene in argon gas sample though a solution containing equal parts of nitrobenzene and o-nitrotoluene. Total pressure in the sample cell during spectra collection was 1-5 torr. All of the data included here were collected in the 660-720 $cm^{-1}$ frequency range. The highly reflective mirrors required to perform cavity ringdown measurements are not, at present, commercially available for this spectral region and thus a more conventional long path absorption cell was incorporated into the system to make these proof-of-concept measurements.

For real world analysis problems, it is necessary to be able to extract concentrations for species of interest (illicit substances and/or medically important diagnostics) from absorption spectra. While there are a number of standard algorithms in the literature for performing such a principal component analysis. See for example, Esler, M. B., D. W. T. Griffith, S. R. Wilson, and L. P. Steele, *Precision Trace Gas Analysis by FTIR Spectroscopy. 1. Simultaneous Analysis of $CO_2$, $CH_4$, $N_2O$, and CO in air*, Analytical Chemistry, 72(1), 206-215 (2000); and Haaland, D. M., R. G. Easterling, and D. A. Vopicka, *Quantiative Spectral Analysis of Multicomponent Samples*, Applied Spectroscopy, 39(1), 73-84 (1985), the current embodiment uses an algorithm originally designed to extract gas phase concentrations from convoluted mass spectral data. Reeve, S. W., W. A. Weimer, and D. S. Dandy, *On the optimization of a dc arcjet diamond chemical vapor deposition reactor*, J. Mater. Res., 11(3), 694-702 (1996). The mass spectral algorithm was built around a fitting function of the form $$S_i = \sum_i F_i C_i \qquad (1)$$

where $S_i$ is the signal strength at a particular mass to charge ratio, $F_i$ the fractional contribution of species i to the signal strength and $C_i$ the concentration of species i. For the mass spectral data problem, the $F_i$ component represents essentially the observed cracking pattern for the species under consideration. In the current embodiment, the fitting function is modified as follows $$S_\lambda = \sum_i F_{\lambda i} C_i + bg_\lambda. \qquad (2)$$

The fractional contribution at each wavelength, $F_\square$, is no longer simply the experimentally observed cracking pattern, but is now a product of the line absorption spectrum for a particular species i, calculated using the known molecular constants from the literature for that species, and a lineshape function. Reeve, S. W., and W. A. Weimer, *Plasma Diagnostics of a direct-current arcjet diamond reactor. II. Optical emission spectroscopy*, J. Vac. Sci. and Technol. A, 13(2), 359-367 (1995). The $bg_\square$ term in the expression above represents the background component in the observed signal. In order to extract the concentration of species contributing to the observed signal, a simulated spectrum is generated via equation (2) using some initial set of concentrations and then is compared with an absorbed spectrum obtained by the multi-color ICOS device. In real time, the simulated spectrum is forced to reproduce the observed spectrum by making a series of iterative changes to the species concentration. In this manner, the species concentration information is extracted from the observed data.

EXAMPLE 1

In one embodiment for skin gas measurements, the infrared source is a He-cooled Pb-salt tunable diode laser from Laser Components; however, almost any tunable laser will be satisfactory. In one embodiment, there are four separate diode lasers mounted in a cryogenic housing (Laser Components L5731 cold head) with a tuning temperature range of 15 K-80 K. The lasers were selected in pairs to provide 80-90% of the tuning range for the 7.5 and 11 micron wavelength region respectively. In other words, two of the lasers were selected for 7.5 microns and two for the 11 micron region. Often the best spectral coverage with Pb-salt diodes is obtained by using pairs of diodes for a given spectral range. In this embodiment, one of the 11 micron diodes has a longitudinal mode near 935 $cm^{-1}$ corresponding to the ammonia QQ (7,3) transition with a spectral resolution of 0.0003 $cm^{-1}$/point in this region.

A double modulation arrangement was implemented to increase measurement sensitivity. With this arrangement, the laser was scanned via an externally generated voltage ramp on a single longitudinal mode. Superimposed on this voltage ramp (SRS DS 345 function generator) is a frequency modulation of 25 KHz which is detected as either a first or second derivative of the absorption signal (see FIG. 10). The sample pressure and flow were controlled and monitored in a low volume 75 meter astigmatic Herriott gas sample cell via a MKS PR 400 Baratron gauge controller, and a MKS 647 multi-gas-flow controller. However, a cavity ringdown cell would work just as well, if not better, and a multi-color multicavity ringdown sample cell (as disclosed herein) will accomplish a plurality of simultaneous real time measurements with an even lower LOD.

The absorption signal was recorded on a measurement channel connected to the PC. The absorption measurements were relatively calibrated using a Geletalon with a free spectral range of 0.049012 $cm^{-1}$. Absolute calibration was obtained using a visual basic program that matches the lines of absorption signal to the HITRAN database spectra of ammonia. The ammonia gas sample for the limit of detection study was purchased from Matheson laboratory (99.9% certification) and a commercially available He probe with a calibrated metering valve from A& N Corporation was used to collect the skin gas emissions. All of the measurements were made utilizing a fundamental rovibrational transition of ammonia near 935 $cm^{-1}$. This particular transition was selected for several reasons, not the least of which is there are minimal interferences from known atmospheric compounds including water vapor, $CO_2$, CO, NO, $NO_2$ and $SO_2$.

Performance Analysis of Pb-Salt Tunable Diode Laser System.

The limit of detection for the Pb-salt tunable diode laser spectrometer was determined by analyzing the background free ammonia rovibrational absorption signal. The background signal was obtained by flowing pure $N_2$ through the astigmatic Herriott cell at a constant flow rate. Several background traces of $N_2$ were recorded and averaged over 500 waveforms in order to evaluate the signal-to-noise ratio. The standard deviation ($\sigma$) of the background traces was computed to be ~$2.7 \times 10^{-4}$. Spectra of $NH_3/N_2$ mixtures at different concentrations were then recorded and averaged to generate a calibration curve. Each $NH_3/N_2$ spectral trace was subtracted from the background trace, where the strongest peak 935.9070 $cm^{-1}$ is selected for calculation of the detection limit. A $3\sigma$ value calculated from the background traces and the slope of the calibration curve gives an estimation of the LOD for the minimum detectable ammonia concentration to be <2 ppb by volume at the 99.97% confidence level.

Ammonia Detection in Skin Gas.

Figure 10:
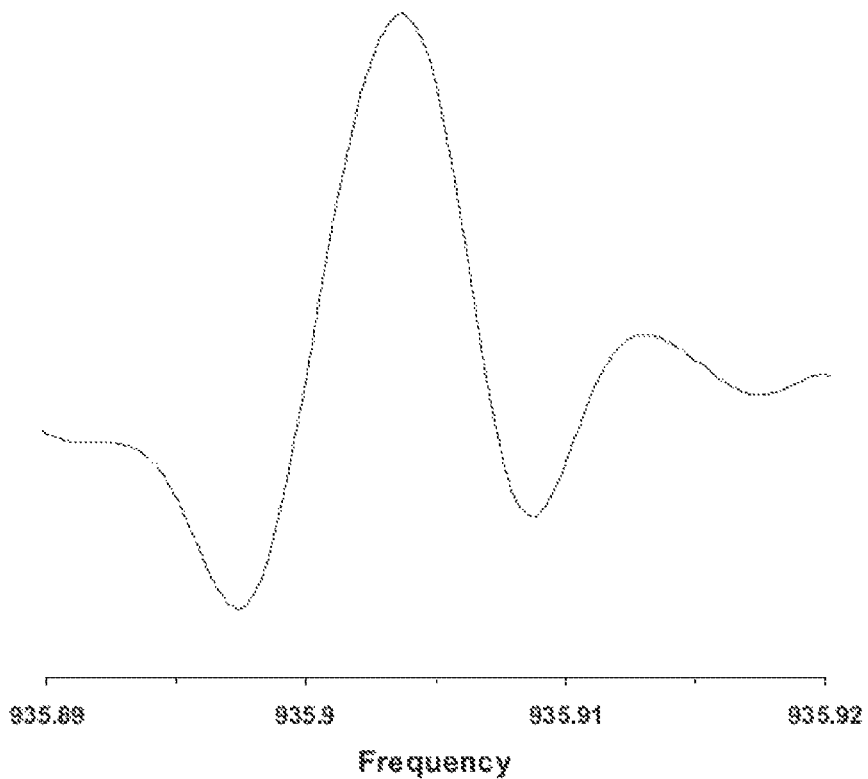
FIG. 10 depicts a representative spectrum of ammonia skin gas emission collected from a human hand.

An ammonia skin gas sample was obtained by washing a hand of a subject with running tap water for one minute, and then spraying it with distilled water for 10 seconds. After wiping the hand with a paper towel, it was left to dry for five minutes. Argon gas was passed though a gas collection probe equipped with a calibrated metering valve for 5-10 minutes immediately prior to passing it over the hand as part of the skin gas emission sample collection. A representative spectrum of the ammonia skin gas emission is shown in FIG. 10. The ammonia concentration giving rise to the signal in FIG. 10 was determined to be 12 ppb based on interpolation with a standard curve. Note, this level of ammonia respiration is consistent with the skin gas emissions from a healthy human subject. (Nose, K., Mizuno, T., Yamane, N., Kondo, T., Ohtani, H., Araki, S., Tsuda, T., "Identification of ammonia in gas emanated from human skin and its correlation with that in blood," Anal. Sci., 21, 1471-1474 (2005).) The use of quantum cascade lasers offers the potential of 10-100 times more sensitivity, which would yield a LOD in parts per trillion.

Besides the aforementioned apparati for accomplishing simultaneous real time detection and analyses of any target molecule(s) in the same gas sample, the invention disclosed herein also includes a method of detecting the presence of at least one gas phase molecule in that sample. Such method generally includes (comprises) the steps of providing a sample of gas phase molecules to said gas receiving means (and cell) of the multi-color absorption spectroscopy apparatus, actuating a plurality of lasers of said apparatus (either before or after introduction of the gas sample into the cell) and detecting the presence of at least one gas phase molecule within the cavity ringdown cell. If only one species of molecule is the target molecule, activation of a plurality of lasers will allow for a plurality of simultaneous tests for that target molecule, thereby enhancing the accuracy of the detection or identification. Alternatively, the plurality of tests will enable the simultaneous comparison of the current gas sample against the profiled norm for that molecule contained in a library of profiles, and/or against any previous profile(s) of that subject (if the computer software is unable to make that dual comparison from the output of a single laser). In the latter instance, any change in concentration of the target molecule of the subject may be determined at that time.

An alternative method would also include obtaining a control sample of environmental gases in the immediate vicinity of the subject, immediately before or after the collection of a gas sample from the subject (such as a breath sample). That environmental control sample would then be analyzed, immediately before (or after) analysis of the subject's sample, by activating at least one laser for scanning its optical cavity immediately before (or after) introduction of the subject's gas sample. Ideally the environmental control sample would be collected almost simultaneously with the collection of the subject's gas sample, but without contamination by the subject's gas sample. It could be analyzed separately, since it takes only a matter of seconds between introduction of any gas sample into the cell (such as with a vacuum "sniffer"), analysis of its cavity ringdown, then evacuation of the cell for introduction of the next sample.

The aforementioned alternatives, with activation of more lasers (and respective optical cavities) within the cavity ringdown cell, will likewise facilitate the detection and/or monitoring of more than one target molecule, Besides detecting the presence of a signature bouquet of a substance, detecting the mere presence of a plurality of target molecules may facilitate the diagnosis of a health condition. Similarly, the monitoring and/or quantification of any change in concentration of the target molecule(s) of the subject may facilitate determination of the effectiveness of any treatment prescribed for the health condition. Alternatively, there may be instances where a false positive or a false negative may be avoided by such simultaneous real time detection and analyses of the target molecule(s) in the same gas sample.

The measurements described here confirm the ability of the disclosed multi-color cavity ringdown based spectrometer system to accomplish simultaneous real time analyses of the same gas sample for detection of (or monitoring the change in concentration of) ammonia, VOCs and/or other skin gases for biomedical applications as well as for evidentiary and/or forensic sampling applications.

Although the present invention has been described and illustrated with respect to preferred embodiments and a preferred user thereof, it is not to be so limited since modifications and changes can be made therein which are within the full scope of the invention.

We claim:

1. A multi-color absorption spectroscopy apparatus for detecting certain molecules in the gas phase sample, comprising:
   (a) a plurality of lasers, each optically coupled to a respective pair of opposing mirrors comprising a cavity ringdown optical cavity, all of said optical cavities housed within the same gas sample cell; and
   (b) a gas receiving means for receiving a sample of gas and providing same to said cell;
   (c) each of said optical cavities outputting the respective radiation to a respective photometric detector for analysis simultaneously with analysis of other respective radiation by another respective photometric detector.

2. A multi-color absorption spectroscopy apparatus of claim 1, said lasers selected from the group consisting of Pb-salt diode lasers, quantum cascade lasers and other tunable laser sources, and combinations thereof capable of continuous wave or non-continuous wave emissions.

3. A multi-color absorption spectroscopy apparatus of claim 1, the molecules in the gas phase sample comprising skin gas.

4. A multi-color absorption spectroscopy apparatus of claim 1, said gas receiving means selected from the group consisting of an exhalation capture chamber, molecular trap and a pre-concentrator bar, and combinations thereof.

5. A multi-color absorption spectroscopy apparatus of claim 1, said gas receiving means comprising a molecular sieve trap.

6. The multi-color absorption spectroscopy apparatus of claim 1, said gas receiving means comprising a tube for receiving the skin gas of a subject.

7. A multi-color absorption spectroscopy apparatus of claim 1, further comprising a computer with analytical programming for comparing the cavity ringdown absorption profile of the sample against a library of cavity ringdown absorption spectrum profiles of the target substance(s).

8. A multi-color absorption spectroscopy apparatus of claim 1, wherein said library includes the cavity ringdown absorption spectrum profile(s) of the sample(s) previously obtained from the test subject(s).

9. A method of detecting the presence of at least one gas phase molecule, comprising the steps of:
   (a) providing the absorption spectroscopy apparatus of claim 1;
   (b) providing a sample of gas phase molecules to said gas receiving means;
   (c) actuating a plurality of the lasers of said apparatus; and
   (d) detecting the presence of at least one gas phase molecule.

10. A method described in claim 9, further comprising the steps of:
    (a) separately providing the cell a sample of the environmental gases near the test subject, collected almost simultaneously with the collection of the subject's gas sample but without contamination by the subject's gas sample;
    (b) separately actuating at least one laser of said apparatus for analysis of said environmental gas sample; and
    (c) detecting the presence or absence of at least one gas phase molecule.

11. A method described in claim 10, wherein said activation of said plurality of lasers scans for detection of more than one species of gas phase molecules.

12. A method described in claim 10, wherein said activation of said plurality of lasers scans for detection of a change in concentration of at least one species of gas phase molecules.

13. A method described in claim 9, said sample of gas phase molecules comprising skin gas.

* * * * *